United States Patent [19]

Schachar

[11] Patent Number: 4,620,979

[45] Date of Patent: Nov. 4, 1986

[54] OPHTHALMOLOGICAL IRRIGATING SOLUTION CONTAINING ASCORBATE

[76] Inventor: Ronald A. Schachar, 7260 Lake View Dr., Denison, Tex. 75020

[21] Appl. No.: 761,791

[22] Filed: Aug. 2, 1985

[51] Int. Cl.$^4$ .................. A61K 31/34; A61K 33/14
[52] U.S. Cl. .................. 424/153; 514/474; 514/912; 424/128
[58] Field of Search ............ 514/474, 912; 424/153, 424/128

[56] References Cited

U.S. PATENT DOCUMENTS

| | | | |
|---|---|---|---|
| 4,201,706 | 5/1980 | Trager et al. | 424/78 |
| 4,336,152 | 6/1982 | Like et al. | 252/106 |
| 4,401,582 | 8/1983 | Sherman | 514/474 |
| 4,443,432 | 4/1984 | Garabedian et al. | 424/127 |

FOREIGN PATENT DOCUMENTS 1239063  10/1964  Fed. Rep. of Germany ...... 514/474

OTHER PUBLICATIONS

The Healing Factor-Vitamin C Against Disease (1972) p. 132-Stone-Grosset & Dunlap: New York.
Chem. Abst., 77:39143p (1972)–Dynakowski et al.
Chem. Abst., 84:65256(s) (1976)–Makabe et al.
Chem. Abst., 91:62643z (1979)–Springen et al.
Chem. Abst., 96:179873u (1982)–Pfister et al.

*Primary Examiner*—Douglas W. Robinson
*Attorney, Agent, or Firm*—Vorys, Sater, Seymour and Pease

[57] ABSTRACT

An ophthalmic irrigation solution for intraocular surgery incorporates, in addition to conventional ions used in such solutions, from about 5.0 to about 30.0 millimoles per liter of ascorbic acid or a physiologically acceptable non-toxic salt thereof. These solutions more nearly approximate the natural composition of the aqueous humor of the eye.

8 Claims, No Drawings

OPHTHALMOLOGICAL IRRIGATING SOLUTION CONTAINING ASCORBATE

BACKGROUND OF THE INVENTION

1. Field of the Invention

This invention relates to irrigation solution for use in ophthalmological surgery, and more particularly to intraocular irrigation solutions having good compatibility with ocular tissues.

2. Description of the Prior Art

In intraocular surgery it is conventional to supply to the surgical field a continuous flow of liquid to replace fluid lost from the interior of the eye. In surgery performed in the anterior chamber of the eye, e.g., in cataract extraction, it is necessary to supply fluid to the anterior chamber to prevent collapse of the chamber with consequent injury to tissues, particularly to the delicate corneal endothelium. Furthermore in some surgical procedures, e.g., phacoemulsification wherein the tissue of the cataractous crystalline lense is broken up, the irrigation fluid serves to carry away fragmented tissue from the surgical site. In posterior chamber surgery, e.g., in vitrectomy, the material removed from the chamber must be replaced with fluid in order to keep the surgical field clear and maintain the volume of the eyeball. In early ophthalmological surgical procedures wherein the time of surgery was relatively short, the intraocular tissue were exposed to the irrigation fluid for a relatively short period of time. Hence, a simple irrigation solution such as physiological saline solution was used. Such as osmotically adjusted solution prevented damage to the tissues due to osmotic shock, did not closely approximate the actual physiological intraocular fluid. As more extensive and longer surgical procedures within the eye began to be performed, the intraocular tisues were exposed for a relatively long time to the irrigation solution, and it became apparent that a solution having a composition closer to that of the natural intraocular fluid, e.g., the aqueous humor of the anterior chamber, was desirable in order to prevent damage to intraocular tissues deprived of their customary surrounding fluid. Accordingly, a number of irrigation solutions have been developed which are believed to be more compatible with the physiology of ocular tissues than physiological saline. For example, lactated Ringer's solution has been used, wherein some of the sodium chloride of physiological saline has been replaced with potassium chloride, calcium chloride and sodium lactate. A further development is balanced salt soluton (BSS), which also includes potassium, calcium and magnesium and an acetate-citrate buffer system, but no lactate. BSS, however, contains no energy source, is slightly hypotonic and has an alkaline pH. Another solution developed for intraocular irrigation is glutathione-bicarbonate-Ringer's solution (GBR), which incorporated reduced glutathione to provide a source of energy for intraocular cells, particularly for cells of the corneal endothelium, in order to maintain these delicate and critical cells in good condition during long surgical procedures. While GBR is an effective intraocular irrigating solution, it is somewhat unstable because the reduced glutathione becomes oxidized during storage and use. In order to overcome this problem a variation of GBR has been developed which uses oxidized glutathione together with glucose to provide a source of energy which the cells may use to produce the reduced glutathione they need.

Each of these irrigation solutions has utility in particular situations. However, ocular tissue also has a need for ascorbate and the aqueous humor is known to contain ascorbate, but the irrigation solutions used hitherto have omitted ascorbate. Hence these solutions have not been able to replace the ascorbate lost during surgery, and a need has continued to exist for an ophthalmic irrigating solution for intraocular surgery which more closely approximates the composition of the natural aqueous humor within the eye.

SUMMARY OF THE INVENTION

The deficiencies of the prior art have now been overcome by an ophthalmic irrigation solution which, in addition to ingredients which contribute to the proper ionic composition for the intended purpose of the intraocular solution, also contains ascorbate in the form of ascorbic acid or a salt thereof, in a concentration to promote the proper functioning of intraocular tissues, a concentration which will ordinarily range from about 5 mg/cc to about 30 mg/cc.

Accordingly, it is an object of the invention to provide an irrigating solution suitable for use in intraocular surgical procedures.

A further object is to provide an intraocular irrigating solution which more nearly approximates the composition of the aqueous humor of the eye.

A further object is to provide an intraocular irrigating solution containing ascorbate.

Further objects of the invention will become apparent from the description which follows.

DETAILED DESCRIPTION OF THE INVENTION AND PREFERRED EMBODIMENTS

According to the invention ascorbate in the form of ascorbic acid or a non-toxic pharmaceutically acceptable salt thereof may be added to conventional ocular irrigating solutions such as Ringer's solution, lactated Ringer's solution, balanced salt solution, GBR or modified GBR containing oxidized glutathione and glucose. The addition of ascorbate in amounts ranging from about 5 mg/cc to about 30 mg/cc provides a concentration of ascorbate in contact with the ocular tissues which approximates the concentration of ascorbate in the natural physiological fluids of the eye such as the aqueous humor. This helps to prevent loss of ascorbate from the tissues and possible injury to the tissues as a result.

An ophthalmic irrigation solution must have an ionic composition which provides an osmotic pressure approximately equal to that of the natural intraocular fluid. For example, the conventional physiological saline solution containing 0.9% by weight of sodium chloride has an osmolarity of about 308 milliosmoles (mOsm). While the exact osmolarity is not critical, it should range from about 270 mOsm to about 310 mOsm. The ingredient present in greatest concentration will be sodium chloride, but its concentration is not in itself critical. Rather, sodium chloride is added to produce the correct osmolarity of the solution. Hence the concentration of sodium chloride will typically range from about 80 millimoles/liter to about 110 millimoles per liter. This amount is substantially less than the conventional amount of 154 millimoles/liter used in normal saline solution, because other ions present in the irrigation solution of this invention contribute to the total osmolarity of the solution.

Calcium is an important ion for maintaining the function of the corneal endothelium, and is present in the irrigation solution of this invention in amounts of from about 1.0 millimole/liter to about 4.5 millimoles per liter. This range generally supplies enough calcium for the requirements of the corneal endothelium during the period of surgery, but it will be understood that the amount may vary within the range of compatiblity with intraocular tissues.

Potassium chloride is included in the irrigation solution of this invention to provide the proper concentration of potassium in the environment of the intraocular cells. The amount of potassium chloride will generally range from about 3.5 millimoles/liter to about 10.5 millimoles per liter. It will be understood that the amount of potassium chloride can vary with special needs of the intraocular tissues.

A typical irrigation solution of this invention based on Ringer's solution will contain about 100 millimoles per liter of sodium chloride, about 4 mM/liter of potassium chloride, about 3 mM/liter of calcium chloride and about 10 to about 25 mM/liter of ascorbate.

If it is desired to prepare a lactated Ringer's type of irrigation solution according to the invention, the solution will incorporate an amount of about 28 millimoles of sodium lactate per liter.

Magnesium chloride will generally be present in the preferred irrigating solutions of the invention in a proportion ranging from about 0.5 millimoles/liter to about 1.5 millimoles per liter.

If it is desired to prepare an improved balanced salt solution according to the invention, the solution will contain about 80 mM/liter of sodium chloride, about 10 mM/liter of potassium chloride, about 4 to 4.5 mM/liter of magnesium chloride hexahydrate, about 1.5 mM/liter of $NaH_2PO_4$, about 29 mM/liter of sodium acetate, about 5.5–6.0 mM/liter of sodium citrate and about 10 to about 25 mM/liter of ascorbate, for example in the form of ascorbic acid.

According to the invention, ascorbate may also be added to an irrigation solution of the glutathione-bicarbonate-Ringer's solution type. Such a solution may contain about 110 mM/liter of sodium chloride, about 4.5–5.0 mM/liter of potassium chloride about 1 mM/liter of calcium chloride, about 0.75 mM/liter of magnesium chloride hexahydrate, about 0.85 mM/liter of sodium dihydrogen phosphate, about 29 mM/liter of sodium bicarbonate, about 0.3 mM/liter of reduced glutathione, about 5 mM/liter of glucose, about 0.5 mM/liter of adenosine, and about 10 to about 25 mM/liter of ascorbate.

It is also possible to add ascorbate to an irrigation solution of the modified GBR type wherein oxidized glutathione is used instead of reduced glutathione and adenosine is omitted. Such a solution will typically include the following ingredients:

|  | millimoles/liter |
| --- | --- |
| NaCl | 105–115 |
| KCl | 4.5–5.0 |
| CaCl$_2$ | 0.9–1.1 |
| MgCl$_2$.6H$_2$O | 0.7–0.85 |
| NaH$_2$PO$_4$ | 0.8–0.9 |
| NaHCO$_3$ | 22–28 |
| Glucose | 4.8–5.2 |
| Glutathione (oxidized) | 0.25–0.35 |

The pH of the ophthalmic irrigation solution of the invention may range from about 6.5 to about 8.2. The will be generally determined by the concentrations of the buffering salts in the solution and may be adjusted by adding acids or bases as is conventional in the art.

The invention will now be further explained by the following examples which are intended to be illustrative and not limiting.

EXAMPLE 1

This example illustrates an irrigation solution according to the invention of the lactated Ringer's solution type.

An aqueous ophthalmic irrigation solution according to the invention is prepared having the following composition

|  | millimoles/liter |
| --- | --- |
| NaCl | 102.00 |
| KCl | 4.00 |
| CaCl$_2$ | 3.00 |
| Sodium lactate | 28.00 |
| Ascorbic acid | 20.00 |

EXAMPLE 2

This example illustrates an irrigation solution according to the invention of the balanced salt solution type.

An aqueous ophthalmic irrigation solution according to the invention is prepared having the following composition

|  | millimoles/liter |
| --- | --- |
| NaCl | 83.80 |
| KCl | 10.10 |
| CaCl$_2$ | 4.32 |
| MgCl$_2$.6H$_2$O | 1.48 |
| Sodium acetate | 28.60 |
| Sodium citrate | 5.78 |
| Ascorbic acid | 15.00 |

EXAMPLE 3

This example illustrates an optalmic irrigation solution according to the invention of the glutathione-bicarbonate-Ringer's solution type.

An aqueous ophthalmic irrigation solution according to the invention is prepared having the following composition

|  | millimoles/liter |
| --- | --- |
| NaCl | 111.56 |
| KCl | 4.82 |
| CaCl$_2$ | 1.04 |
| MgCl$_2$.6H$_2$O | 0.78 |
| NaH$_2$PO$_4$ | 0.86 |
| NaHCO$_3$ | 29.20 |
| Glucose | 5.01 |
| Adenosine | 0.50 |
| Glutathione (reduced) | 0.30 |
| Ascorbic acid | 25.00 |

EXAMPLE 4

This example illustrates an ophthalmic irrigation solution of this invention of the modified glutathione-bicarbonate-Ringer's solution type.

An aqueous ophthalmic irrigation solution according to the invention is prepared having the following composition

|  | millimoles/liter |
|---|---|
| NaCl | 111.56 |
| KCl | 4.82 |
| CaCl$_2$ | 1.04 |
| MgCl$_2$.6H$_2$O | 0.78 |
| NaH$_2$PO$_4$ | 0.86 |
| NaHCO$_3$ | 25.00 |
| Glucose | 5.01 |
| Glutathione (oxidized) | 0.30 |
| Ascorbic acid | 20.00 |

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A method for maintaining substantially normal ascorbate levels in the ocular tissue of an eye subjected to an intraocular surgical procedure, which comprises irrigating the eye with an ophthalmic aqueous irrigating solution having the following composition:

|  | millimoles/liter |
|---|---|
| NaCl | 80.0–115.0 |
| KCl | 3.5–10.5 |
| CaCl$_2$ | 1.0–4.5 |
| MgCl$_2$.6H$_2$O | 0.0–1.5 |
| NaH$_2$PO$_4$ | 0.0–0.9 |
| NaHCO$_3$ | 0.0–30.0 |
| Glucose | 0.0–5.5 |
| Adenosine | 0.0–0.5 |
| Glutathione | 0.0–0.3 |
| Sodium acetate | 0.0–29.0 |
| Sodium citrate | 0.0–6.0 |
| Sodium lactate | 0.0–30.0 |
| Ascorbate | 5.0–30.0 |

2. The method of claim 1 wherein said ascorbate is supplied in the form of ascorbic acid.

3. The method of claim 1 wherein said ascorbate is supplied in the form of a pharmaceutically acceptable non-toxic salt of ascorbic acid.

4. The method of claim 1 wherein said irrigating solution has the following composition:

|  | millimoles/liter |
|---|---|
| NaCl | 102.00 |
| KCl | 4.00 |
| CaCl$_2$ | 3.00 |
| Sodium lactate | 28.00 |
| Ascorbic acid | 20.00 |

5. The method of claim 1 wherein said irrigating solution has the following composition:

|  | millimoles/liter |
|---|---|
| NaCl | 83.80 |
| KCl | 10.10 |
| CaCl$_2$ | 4.32 |
| MgCl$_2$.6H$_2$O | 1.48 |
| Sodium acetate | 28.60 |
| Sodium citrate | 5.78 |
| Ascorbic acid | 15.00 |

6. The method of claim 1 wherein said irrigating solution has the following composition:

|  | millimoles/liter |
|---|---|
| NaCl | 111.56 |
| KCl | 4.82 |
| CaCl$_2$ | 1.04 |
| MgCl$_2$.6H$_2$O | 0.78 |
| NaH$_2$PO$_4$ | 0.86 |
| NaHCO$_3$ | 29.20 |
| Glucose | 5.01 |
| Adenosine | 0.50 |
| Glutathione (reduced) | 0.30 |
| Ascorbic acid | 25.00 |

7. The method of claim 1 wherein said irrigating solution has the following composition:

|  | millimoles/liter |
|---|---|
| NaCl | 105–115 |
| KCl | 4.5–5.0 |
| CaCl$_2$ | 0.9–1.1 |
| MgCl$_2$.6H$_2$O | 0.7–0.85 |
| NaH$_2$PO$_4$ | 0.8–0.9 |
| NaHCO$_3$ | 22–28 |
| Glucose | 4.8–5.2 |
| Glutathione (oxidized) | 0.25–0.35 |
| Ascorbic acid | 15–25 |

8. The method of claim 5 wherein said irrigating solution has the following composition:

|  | millimoles/liter |
|---|---|
| NaCl | 111.56 |
| KCl | 4.82 |
| CaCl$_2$ | 1.04 |
| MgCl$_2$.6H$_2$O | 0.78 |
| NaH$_2$PO$_4$ | 0.86 |
| NaHCO$_3$ | 25.00 |
| Glucose | 5.01 |
| Glutathione (oxidized) | 0.30 |
| Ascorbic acid | 20.00 |

* * * * *